US007955230B1

(12) United States Patent
Al-Oboudi

(10) Patent No.: US 7,955,230 B1
(45) Date of Patent: Jun. 7, 2011

(54) FOOT SLIDER THERAPY DEVICE

(76) Inventor: Waleed Al-Oboudi, Torrance, CA (US)

( * ) Notice: Subject to any disclaimer, the term of this patent is extended or adjusted under 35 U.S.C. 154(b) by 0 days.

(21) Appl. No.: 11/242,595

(22) Filed: Oct. 3, 2005

Related U.S. Application Data

(60) Provisional application No. 60/615,222, filed on Oct. 1, 2004.

(51) Int. Cl.
*A63B 23/10* (2006.01)
*A63B 71/00* (2006.01)
*A61F 5/00* (2006.01)

(52) U.S. Cl. ............................ 482/79; 482/139; 602/23

(58) Field of Classification Search .............. 602/27–30, 602/23; 482/74, 79, 44, 47–49; 128/882; 601/27; 36/132, 136; 119/770; 434/247, 434/250, 255; 5/624
See application file for complete search history.

(56) References Cited

U.S. PATENT DOCUMENTS 735,860 A * 8/1903 Darby .............................. 602/29
2,282,307 A * 5/1942 Davis .............................. 606/237
2,754,121 A * 7/1956 Jupiter .............................. 434/250
2,761,223 A * 9/1956 Legeai .............................. 434/255
2,860,424 A * 11/1958 McKinnou .............................. 434/255
3,527,209 A * 9/1970 Baker .............................. 602/28
3,713,437 A * 1/1973 Wiedmer .............................. 601/27
4,728,103 A * 3/1988 Fulton .............................. 482/125
5,582,579 A * 12/1996 Chism et al. .............................. 601/27
6,206,807 B1 * 3/2001 Cowans et al. .............................. 482/79
6,325,023 B1 * 12/2001 Elnatan .............................. 119/770
6,361,514 B1 * 3/2002 Brown et al. .............................. 602/23
6,361,516 B1 * 3/2002 Hamel .............................. 602/27
6,666,798 B2 * 12/2003 Borsheim .............................. 482/54

* cited by examiner

*Primary Examiner* — Allana Lewin
(74) *Attorney, Agent, or Firm* — Knobbe, Martens, Olson & Bear LLP

(57) ABSTRACT

A device for promoting proper walking-related muscle development is disclosed. In various embodiments, the device can be worn on the foot of a patient undergoing walking therapy. The device includes a toe section that can be secured to the foot, and provides a relatively slidable surface that allows relatively easy sliding of the toe section on the floor. Such a configuration facilitates easier execution of a step movement that promotes walking-related muscle development. The device can also include one or more attachments configured to allow a therapist to assist and/or guide the steps of the patient. In one embodiment, the attachment can be a loop attached to the toe section so that the therapist can insert his/her foot and guide/assist the patient's steps.

4 Claims, 2 Drawing Sheets

FOOT SLIDER THERAPY DEVICE

RELATED APPLICATIONS

This Application claims the benefit of U.S. Provisional Application Ser. No. 60/615,222, filed Oct. 1, 2004, which is hereby incorporated by reference in its entirety.

BACKGROUND OF THE INVENTION

1. Field of the Invention

This invention relates generally to orthotic devices, and more particularly, to a foot device that improves a rehabilitating patient's ability to take steps and develop proper muscular advancement.

2. Description of the Related Art

When a person's walking ability is impaired, it is common for that person to rotate the impaired leg and drag the corresponding foot sideways. While such a walking posture may feel more comfortable at the time, it does not promote proper muscle repair or development.

When a person is being rehabilitated from an injury, illness, and the like, it is important that during the therapy, the person's walking posture be correct so as to promote proper muscle development and advancement.

For these reasons, there is an ongoing need for a device that promotes improved muscle development for patients undergoing walking therapy.

SUMMARY OF THE INVENTION

The foregoing needs can be addressed by a device for promoting proper walking-related muscle development. In various embodiments, the device can be worn on the foot of a patient undergoing walking therapy. The device includes a toe section that can be secured to the foot, and provides a relatively slidable surface that allows relatively easy sliding of the toe section on the floor. Such a configuration facilitates easier execution of a step movement that promotes walking-related muscle development. The device can also include one or more attachments configured to allow a therapist to assist and/or guide the steps of the patient. In one embodiment, the attachment can be a loop attached to the toe section so that the therapist can insert his/her foot and guide/assist the patient's steps.

One embodiment of the present disclosure relates to an orthotic device for promoting development of muscles associated with walking. The device includes a toe section that is configured to receive a toe portion of a foot. The device further includes a foot-securing device that secures the foot to the toe section. The device further includes one or more assistance devices attached to the toe section. The assistance device is configured to allow assistance or guidance of walking movements of a person wearing the orthotic device by another person.

In one embodiment, the toe section comprises a bottom plate coupled to a front wall and two side walls so as to define a space dimensioned to receive the toe portion of the foot. In one embodiment, the front wall and the two side walls are arranged in substantially square configuration relative to each other and with respect to the bottom plate.

In one embodiment, the bottom plate includes an external surface that allows sliding of the bottom plate relative to a surface of a floor.

In one embodiment, the foot-securing device comprise one or more straps that allow securing of different sized feet to the toe section.

In one embodiment, the one or more assistance devices comprise one or more loops attached to the toe section. The one or more loops are dimensioned to receive the foot of the another person. In one embodiment, the one or more loops comprise a loop attached to the top portion of the toe section, the loop facing sideways so as to allow insertion of the foot of the another person from the side of the person. In one embodiment, the one or more loops comprise a loop attached to the front portion of the toe section so as to allow insertion of the foot of the another person from the front of the person.

BRIEF DESCRIPTION OF THE DRAWINGS

These and other aspects, advantages, and novel features of the present teachings will become apparent upon reading the following detailed description and upon reference to the accompanying drawings. In the drawings, similar elements have similar reference numerals.

DETAILED DESCRIPTION OF CERTAIN EMBODIMENTS

The systems, methods, and devices of the invention each have several aspects, no single one of which is solely responsible for its desirable attributes. Without limiting the scope of this invention, its more prominent features will now be discussed.

The present disclosure generally relates to various embodiments of a device that provide advantages that include, for example, inhibiting rotation of the leg and facilitate re-development of advancement ability for individuals who suffer from stroke or other neurological disorders.

Figure 1:
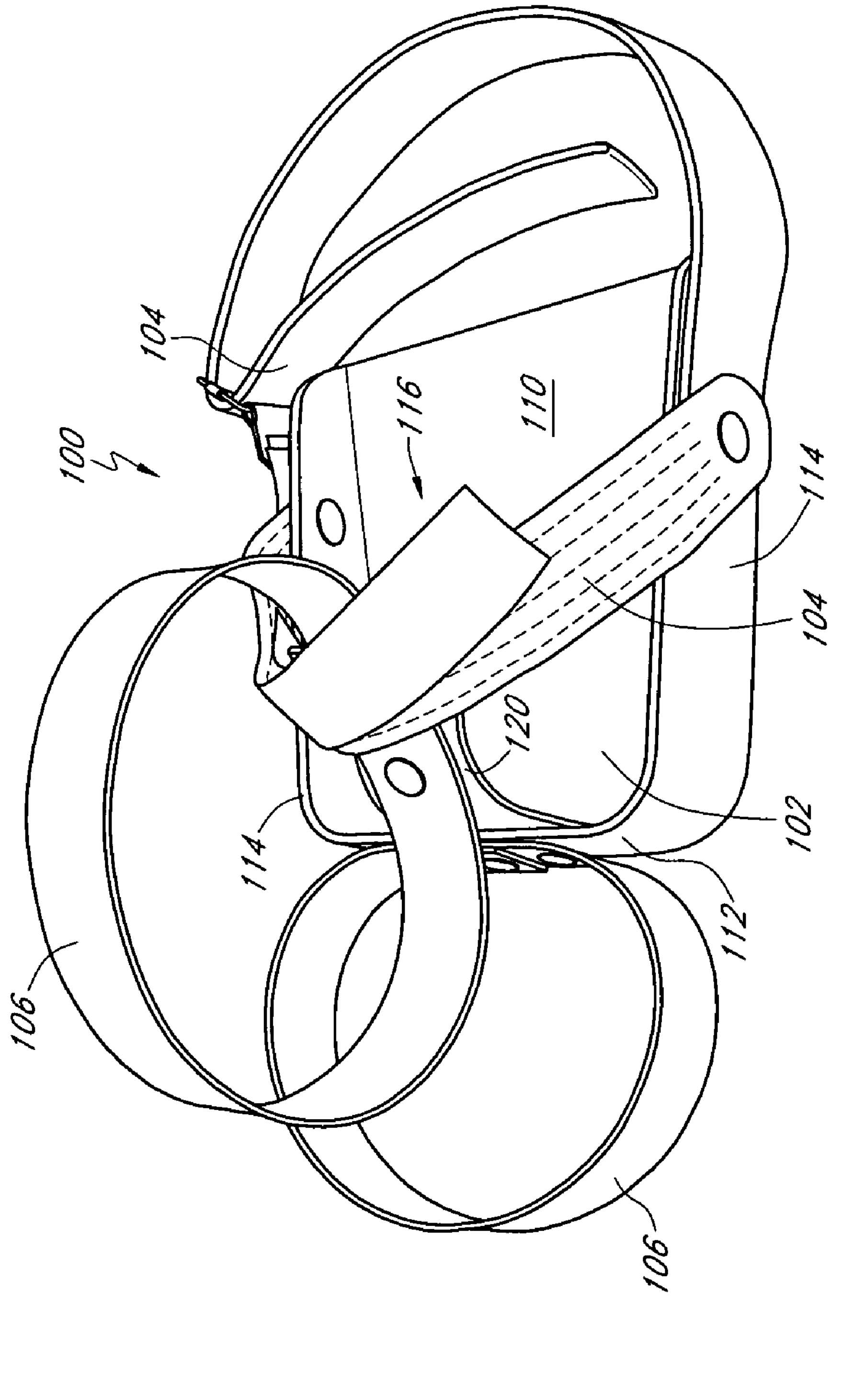
FIG. 1 is a perspective view of one embodiment of a foot slider therapy device.

FIG. 1 shows one embodiment of a foot slider device 100 that can be worn by a patient during rehabilitation. When worn, the foot slider device 100 inhibits rotation of the patient's leg and thereby improves the patient's ability to take steps and develop proper muscular advancement.

In one embodiment, the device 100 includes a toe section 102 configured to receive and support the toe section of a person. In one embodiment, the toe section 102 is substantially square.

The example substantially square toe section 102 helps the person maintain a correct position for muscular advancement and inhibit external and/or internal rotation of the leg. To achieve such functionality, one embodiment of the device 100 can include one or more straps 104 or other suitable foot-securing devices to secure the person's foot to the device 100. In one embodiment, the exterior surface of the device 100 comprises a material that generates very little traction such that the device 100 can move or slide over a surface when very little force is applied. Thus, the person wearing the device 100 can slide the front portion of the foot with a reduced effort and maintain a proper walking posture that promotes muscular advancement. By allowing such walking posture with a reduced effort, the patient's tendency of rotating the leg and dragging the foot sideways can be reduced.

As further shown in FIG. 1, one embodiment of the device 100 can also include one or more attachments 106 configured to allow a therapist or another person to assist the patient's steps.

Figure 2:
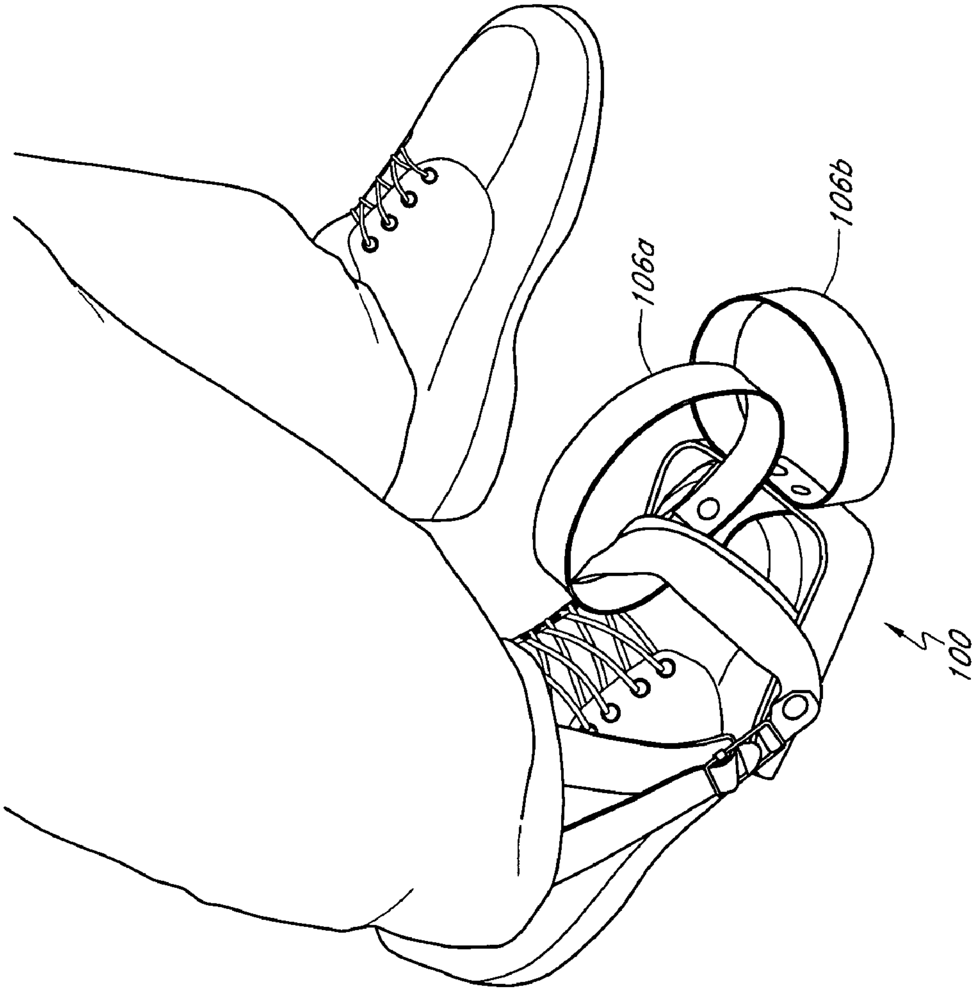
FIG. 2 illustrates the foot slider therapy device of FIG. 1 in use.

FIG. 2 shows the example foot slider device 100 worn by a patient. A therapist or another person (not shown) standing next to the patient (for example, on the right side of the patient) can assist and/or guide the patient's steps by inserting a foot into the example attachment 106*a*. In one embodiment the attachment 106*a* is a loop attached to the top portion of the toe section 102 of the device 100. The loop 106*a* defining a first opening can face sideways, extending outwardly from the toe section 102 in a sideways configuration, so that the therapist can insert his/her foot into the loop 106*a* substantially orthogonally and guide and/or assist the patient's steps.

In one embodiment, an attachment 106*b* defining a second opening can be positioned at a location front of the toe section 102 disposed orthogonally relative to the loop 106*a* and the first opening to allow similar guidance and/or assistance from the front of the front of the patient. Thus, one can see that in various embodiments, one or more attachments that allow guidance and/or assistance of the patient's steps can be mounted at various locations on or about the foot slider device 100.

Using such a guidance/assistance attachment, a therapist can guide the steps of the patient by preventing the patient's leg from rotating. The therapist can also assist the patient's steps, for example, by gently boosting the upward motion of the foot during the steps.

In one embodiment, the toe section 102 can be formed from resilient materials such as plastic. In one embodiment, the foot-securing devices 104 can include straps having Velcro strips that allows for adjustable fits of various sized feet. In one embodiment, the guide/assist attachments 106 can include plastic loops attached to various locations of the toe section 102.

In one embodiment, the toe section 102 includes a bottom plate 110 coupled to a front wall 112 and two side walls 114 so as to define a space 116 dimensioned to receive the toe portion of a foot. In one embodiment, the front wall 112 and the side walls 114 are arranged in a substantially square configuration relative to each other and with respect to the bottom plate 110.

In one embodiment, the toe section 102 further includes a top strap 120 that extends up and rearwards from the front wall 112. In one embodiment, the top strap 120 provides an attachment location for the example loop 106*a* (FIG. 2). In one embodiment, the front wall 112 provides an attachment location for the example loop 106*b*. In one embodiment, the side walls 114 also provide attachment locations for the example straps 104. In one embodiment, one of the one or more straps 104 is fed through the example loop 106*b* so that the strap provides securing function of the toe portion of the foot to the toe section 102, as well as provide additional securing of the loop 106*a* to the toe section 102.

Although the above-disclosed embodiments have shown, described, and pointed out the fundamental novel features of the invention as applied to the above-disclosed embodiments, it should be understood that various omissions, substitutions, and changes in the form of the detail of the devices, systems, and/or methods shown may be made by those skilled in the art without departing from the scope of the invention. Consequently, the scope of the invention should not be limited to the foregoing description, but should be defined by the appended claims.

What is claimed is:

1. A method for guiding and assisting the steps of a patient with impaired walking ability implemented by a foot slider device, the method comprising:

providing a foot slider device configured to receive the patient's foot, said device having a toe section configured to receive and support the toe section of the patient in a manner that inhibits rotation of the patient's leg and a first loop that is disposed above the toe section and extends outwardly from the toe section in a sideways configuration, wherein the first loop is dimensioned to allow insertion of a therapist's foot such that the therapist's foot can be positioned substantially orthogonally relative to the patient's foot, wherein the toe section provides a relative slidable surface that guides the patient's step from the front of the patient's foot by sliding the front portion of the patient's foot, the configuration of the toe section reduce the patient's tendency of rotating the leg and dragging the foot sideways;

inserting the therapist's foot into the loop; and moving the patient's foot in a manner such that the loop boosts the upward motion of the patient's foot as the patient takes a step.

2. The method of claim 1, wherein the foot slider device further comprises a second loop, said second loop is attached to the toe section and disposed orthogonally relatively to the first loop.

3. The method of claim 2, wherein the loop is attached to the front portion of the toe section of the device.

4. The method of claim 1, wherein the toe section of the foot slider device comprises a bottom plate, a front wall and two side walls, said bottom plate is coupled to the front wall and two side walls, wherein the front wall and the two side walls are arranged in substantially square configuration, wherein the substantially square toe section inhibits rotation of the leg.

* * * * *